United States Patent
Bevier et al.

(10) Patent No.: US 6,190,393 B1
(45) Date of Patent: Feb. 20, 2001

(54) DIRECT STENT DELIVERY CATHETER SYSTEM

(75) Inventors: Richard H. Bevier, Bronxville, NY (US); Peter G. Piferi, Plantation; Cesar L. Silva, Pembroke Pine, both of FL (US)

(73) Assignee: Cordis Corporation, Miami Lakes, FL (US)

( * ) Notice: Under 35 U.S.C. 154(b), the term of this patent shall be extended for 0 days.

(21) Appl. No.: 09/277,885

(22) Filed: Mar. 29, 1999

(51) Int. Cl.[7] .................................................. A61M 25/10
(52) U.S. Cl. ........................ 606/108; 623/1.11; 604/96.1
(58) Field of Search ................................. 606/108, 191, 606/192, 194, 198; 604/101, 96.1, 264, 280, 171, 103; 623/1.23, 1.11

(56) References Cited

U.S. PATENT DOCUMENTS

| | | | |
|---|---|---|---|
| 5,242,399 | * | 9/1993 | Lau et al. ............................... 604/104 |
| 5,290,295 | * | 3/1994 | Querals et al. ....................... 606/108 |
| 5,453,090 | * | 9/1995 | Martinez et al. ...................... 604/53 |
| 5,534,007 | * | 7/1996 | St. Germain et al. ................ 606/108 |
| 5,603,698 | * | 2/1997 | Roberts et al. ....................... 604/104 |
| 5,628,755 | * | 5/1997 | Heller et al. .......................... 606/108 |
| 5,690,644 | * | 11/1997 | Yurek et al. ........................... 606/108 |
| 5,702,418 | * | 12/1997 | Ravenscroft .......................... 606/198 |
| 5,843,092 | * | 12/1998 | Heller et al. .......................... 606/108 |
| 5,980,533 | * | 2/2000 | Holman ................................. 606/108 |
| 6,019,777 | * | 2/2000 | Holman ................................. 606/108 |

* cited by examiner

*Primary Examiner*—Gene Mancene
*Assistant Examiner*—Michael B. Priddy

(57) ABSTRACT

A stent delivery system for medical treatment of a patient and for performing primary or direct stenting includes a balloon catheter, a stent, a sheath, and a flexible tapered introducer tip. The balloon catheter has a hub, shaft, and inflatable balloon, as well as a tubular stent mounted about the deflated balloon and crimped to an initial diameter. The introducer tip is affixed to the distal end of the balloon catheter and tapers to a maximum outer diameter equal to the crimped stent outer diameter plus the sheath wall thickness. The composite sheath has a multiple diameter design with a distal portion adapted to retractably cover the crimped stent, and a proximal portion having a smaller diameter. This smaller diameter enables greater flow of a radiopaque contrast fluid around the outside of the proximal sheath and through the inside of a guiding catheter, thus providing the system with a high visibility capability. The introducer tip defines a shoulder against which the sheath can push in a distal direction, assisting the stent delivery system to perform primary stent delivery without a preliminary angioplasty procedure.

6 Claims, 5 Drawing Sheets

DIRECT STENT DELIVERY CATHETER SYSTEM

BACKGROUND AND SUMMARY OF THE INVENTION

1. Technical Background

The present invention relates generally to medical devices, and more particularly to a stent delivery catheter system.

2. Discussion

Catheter systems are used in a variety of therapeutic applications, including many vascular treatments. Various types of catheters are available, such as balloon catheters for procedures such as angioplasty. Angioplasty can be used to treat vascular disease, in which blood vessels are partially or totally or partially blocked or narrowed by a lesion or stenosis. By way of example, the present invention will be described in relation to coronary and peripheral angioplasty and other vascular treatments. The coronary procedure is often referred to as PTCA, which stands for "percutaneous transluminal coronary angioplasty". However, it should be understood that the present invention relates to any stent delivery system having the features of the present invention, and is not limited to angioplasty.

Most balloon catheters have a relatively long and flexible tubular shaft defining one or more passages or lumens, and an inflatable balloon attached near one end of the shaft. This end of the catheter where the balloon is located is customarily referred to as the "distal" end, while the other end is called the "proximal" end. The balloon is connected to one of the lumens extending through the shaft for the purpose of selectively inflating and deflating the balloon. The other end of this inflation lumen leads to a hub coupling at the other end for connecting the shaft lumens to various equipment. Examples of this type of balloon catheter are shown in U.S. Pat. No. 5,304,197, entitled "Balloons For Medical Devices And Fabrication Thereof," issued to Pinchuk et al. on Apr. 19, 1994; and also in U.S. Pat. No. 5,370,615, entitled "Balloon Catheter For Angioplasty," issued to Johnson on Dec. 6, 1994.

A common treatment method for using such a balloon catheter is to advance the catheter into the body of a patient, by directing the catheter distal end percutaneously through an incision and along a body passage until the balloon is located within the desired site. The term "desired site" refers to the location in the patient's body currently selected for treatment by a health care professional. After the balloon is disposed within the desired site, it can be selectively inflated to press outward on the body passage at a relatively high pressure to a relatively constant diameter, in the case of an inelastic or non-compliant balloon material.

This outward pressing of a constriction or narrowing at the desired site in a body passage is intended to partially or completely re-open or dilate that body passageway or lumen, increasing its inner diameter or cross-sectional area. The narrowing of the body passageway lumen is called a lesion or stenosis, and may be formed of hard plaque or viscous thrombus. In the case of a blood vessel, this procedure is referred to as angioplasty. The objective of this procedure is to increase the inner diameter or cross-sectional area of the vessel passage or lumen through which blood flows, to encourage greater blood flow through the newly expanded vessel.

In some cases, a flexible cylinder or scaffold made of metal or polymers, which is called a stent, may be permanently implanted into the vessel following an angioplasty procedure. The stent tends to hold the lumen open longer, to reinforce the vessel wall and improve blood flow.

To improve efficiency and reduce time required for the vascular procedure, it is desirable to combine these two procedures, angioplasty and stent deployment. This combined procedure may be referred to as "primary stenting" or "direct stenting." Several benefits may be realized by employing such a combined procedure, including reduced time of the procedure, less intervention, and fewer medical devices inserted into the patient's body.

During a primary stenting procedure, an initial angioplasty is not performed. Rather, a modified stent delivery system is used to cross or traverse a lesion or stenosis, expand the desired site in a fashion similar to angioplasty and deploy a stent, all in a single, unified procedure. In this direct stenting procedure, the stent delivery system is first advanced within the patient's body until the stent is located within the desired site, where the lesion or stenosis is present.

Of course, the operating environment for the stent delivery system may be more difficult when the initial broadening angioplasty or "pre-dilatation" is absent. In other words, the vessel may be narrowed or blocked, and the lesion or stenosis may even be calcified or hardened. The stent delivery system should preferably have a mechanism for more successfully traversing a more difficult environment. After crossing the lesion, the stent delivery system balloon is inflated to expand the stent, followed by deflation of the balloon and withdrawal of the stent delivery system.

Previously known stent delivery systems may have been merely a balloon catheter having a stent mounted and crimped onto the deflated balloon. Such elegantly simple devices have been sufficient for many applications, but a more sophisticated system may be desirable in more challenging cases and environments.

Friction forces may tend to cause a crimped stent to slip in a proximal direction while the catheter system is advanced, or to slip in a distal direction if the physician decides to withdraw the stent without deploying it. It is of course desirable to retain the stent securely in the proper position.

The stent delivery system should also preferably protect the stent from damage or deformation during this period. It is further desirable that the stent delivery system should be able to push through and traverse as many different anatomical arrangements and stenosis configurations as possible. Moreover, the stent delivery system should preferably have a positive mechanism for holding and then releasing, expanding, and deploying the stent at the desired site.

Accordingly, the stent delivery system also desirably includes a mechanism for securing the stent in the form of a sheath, capable of completely covering the crimped stent during insertion. This sheath is permanently mounted about the balloon catheter, yet able to slide in a proximal direction from the stent-covering position, to uncover the stent during inflation of the balloon and expansion of the stent.

Prior stent delivery systems were often designed for the smallest possible outer diameter or profile at the distal end. The small profile was preferred for access into small vessels following angioplasty. In addition, prior stent delivery systems generally provided distal tips which were as short as possible, sometime extending only a few millimeters beyond the distal balloon leg.

However, the present direct stent delivery system preferably contradicts these prior design ideas by providing an enlarged and lengthened, flexible tapering tip. This distal tip tapers gradually up to an outer diameter preferably equal to the largest outer diameter of the entire system, and tends to gently widen any particularly narrow stenoses.

In addition, the sheath should have sufficient wall thickness to push distally against a portion of the flexible tip, to increase the column strength of the stent delivery system. This enhanced "pushability" better enables the stent delivery system to traverse and cross a lesion or stenosis.

In addition, the stent delivery system should provide for high visibility under fluoroscopy. Often the stent delivery system will be used in conjunction with an outer guiding catheter, which surrounds and guides the stent delivery system into a position near the desired site. The visibility of the stent delivery system may be affected by the size of the lumen through which radiopaque contrast fluid is injected. This fluid shows up on a fluoroscope, and is generally injected through the annular space between the inner wall of the guiding catheter and the outer surface of the stent delivery system. The visibility of the stent delivery system under fluoroscopy can therefore preferably be increased by reducing the outer diameter of the stent delivery system along a major portion of all of its length.

Accordingly, the present invention preferably provides a direct stent delivery system for delivering and deploying a stent. This stent delivery system preferably also provides enhanced stent position retention, as well as stent protection, during longitudinal movement of the catheter.

The stent delivery system also is preferably capable of traversing total vessel occlusions, preferably having enhanced pushability and a positive stent release mechanism.

The stent delivery system also preferably has a high visibility arrangement for the injection of radiopaque contrast medium.

These and various other objects, advantages and features of the invention will become apparent from the following description and claims, when considered in conjunction with the appended drawings.

DETAILED DESCRIPTION OF THE PREFERRED EMBODIMENT

Figure 1:
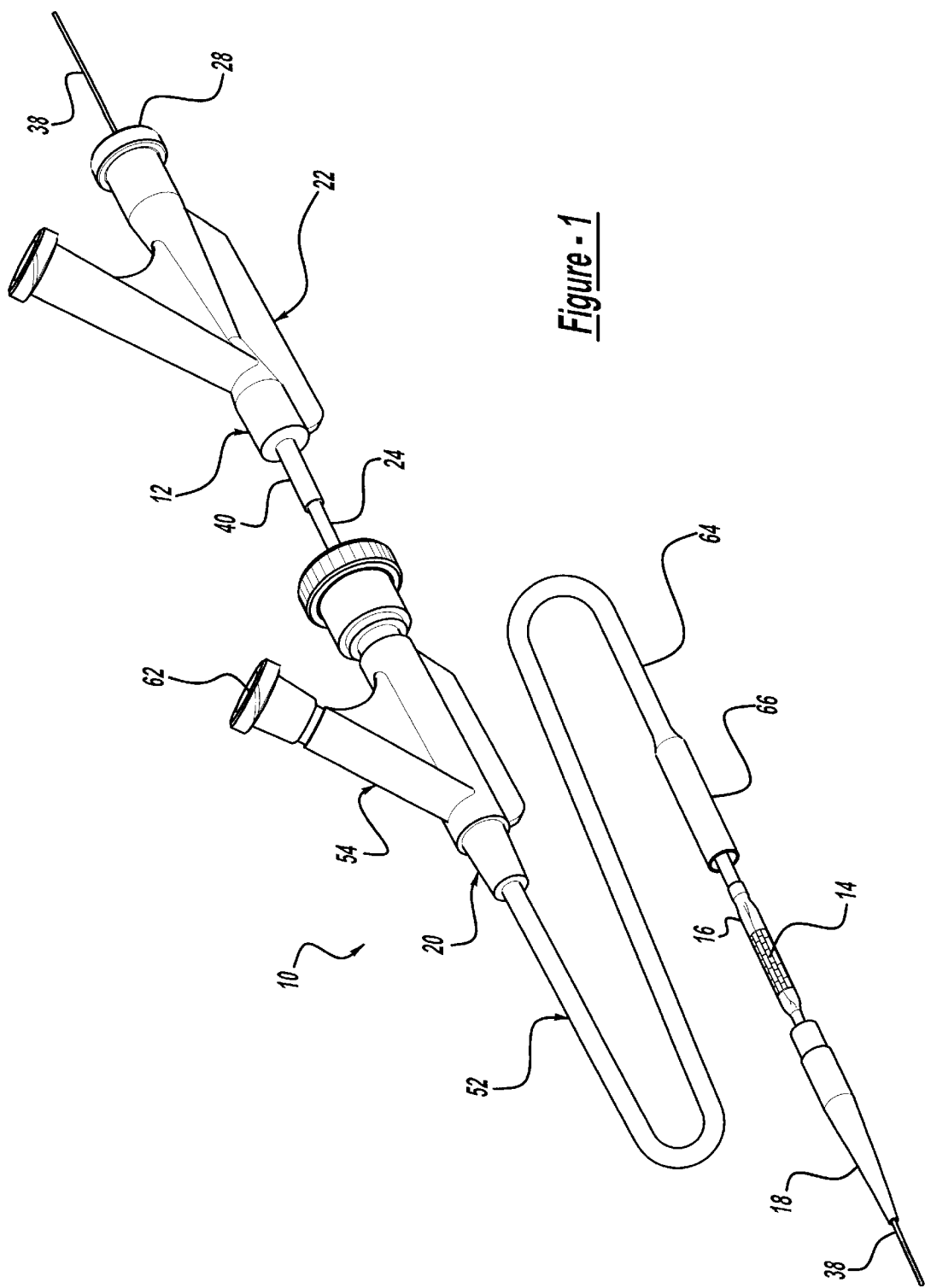
FIG. 1 is an external perspective view of a stent delivery system, arranged according to the principles of the present invention.
Figure 2:
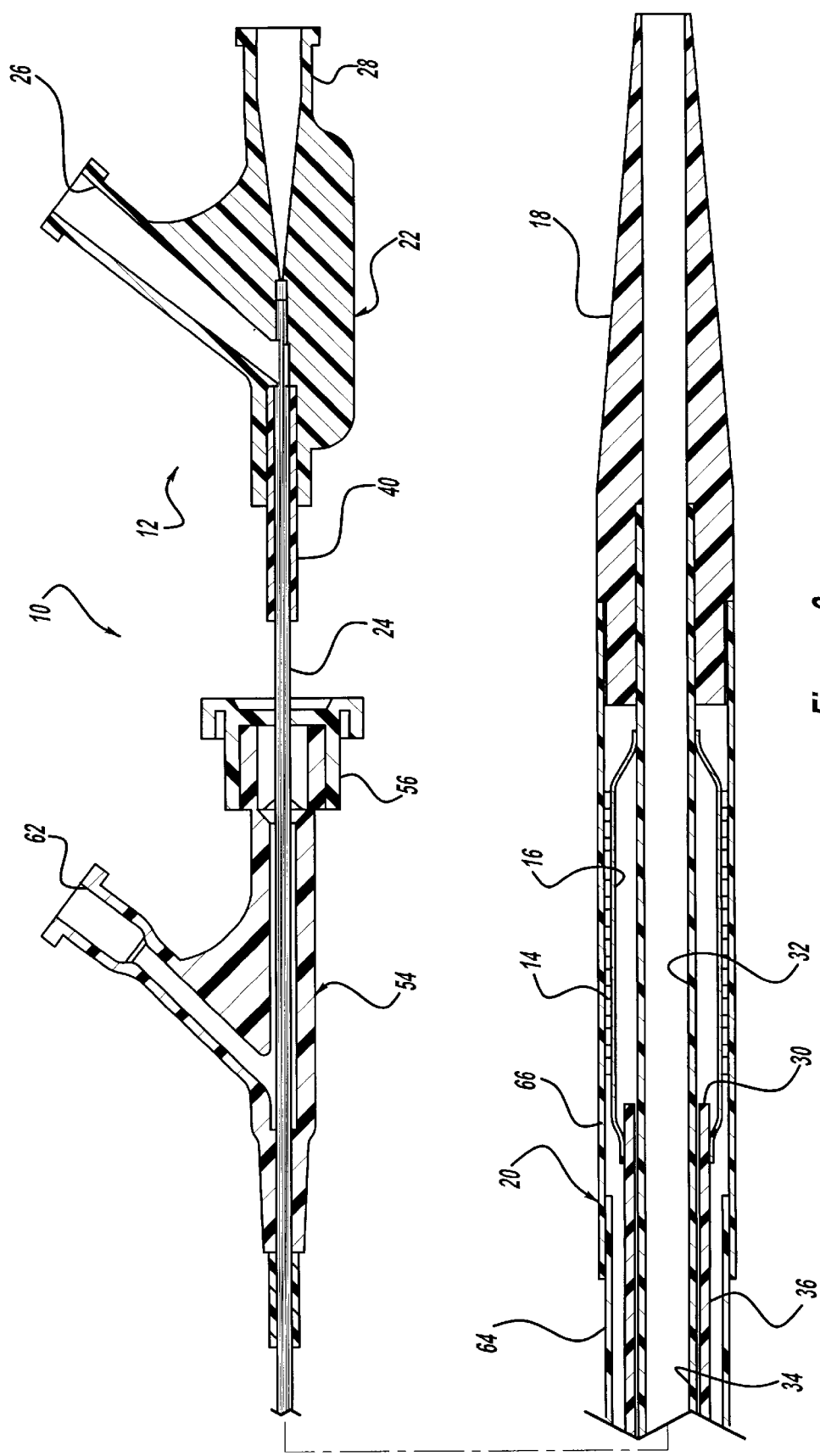
FIG. 2 is a longitudinal cross-section view of the stent delivery system of FIG. 1, shown in an initial configuration.
Figure 3:
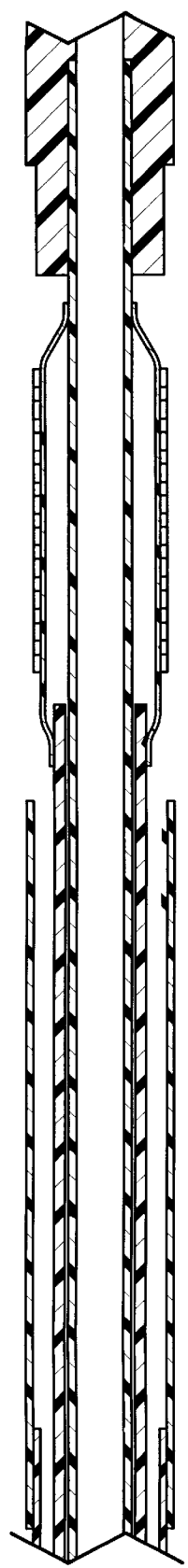
FIG. 3 is a partial longitudinal cross-section view of the stent delivery system of FIG. 2, wherein the sheath is partially retracted.

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, a stent delivery system is depicted, with one of the preferred embodiments of the present invention being shown generally at 10. The stent delivery system 10 illustrated in FIG. 1 includes a balloon catheter 12, a stent 14 crimped around a deflated balloon 16, a flexible tapered introducer tip 18, and a sheath 20. The balloon catheter 12 has an inflatable balloon 16 and a balloon catheter hub 22, each affixed near opposite ends of a flexible balloon catheter shaft 24. The inflatable balloon 16 is located near the distal end of the balloon catheter shaft 24, and the balloon catheter hub 22 is near the proximal end.

The balloon catheter hub 22 provides a maneuvering handle for the health care professional, as well as an inflation port 26 and a guidewire port 28. Either or both the inflation port 26 or the guidewire port 28 may have a coupling, accompanied by a luer-lock fitting for connecting an inflation lumen 30 to a source of pressurized inflation fluid (not shown) in the conventional manner.

The balloon catheter shaft 24 defines one or more passages or lumens 30 and 32 extending through the shaft, one of which is an inflation lumen 30 connected to the balloon 16 to selectively inflate and deflate it. The inflation lumen 30 provides fluid communication between the interior of the balloon 16 at the distal end of the inflation lumen 30 and the hub inflation port 26.

In the illustrated embodiment, at least a portion of the balloon catheter shaft 24 is constructed of an inner and outer tubular body 34 and 36. The inner body 34 defines a guidewire lumen 32, while the inflation lumen 30 is defined by the annular space between the inner and outer tubular bodies 34 and 36. The guidewire lumen 32 is adapted to receive an elongated flexible guidewire 38 in a sliding fashion through a proximal guidewire port 28 in the balloon catheter hub 22, and may ultimately extend out through a distal guidewire port 28 defined at a distal end of the inner body 34. The guidewire 38 and balloon catheter 12 may thus be advanced or withdrawn independently, or the balloon catheter 12 may be guided along a path selected with the guidewire 38.

The balloon catheter shaft 24 may of course have various configurations instead of this coaxial design shown in the drawings, including a single extruded multi-lumen tube defining any suitable number of parallel side-by-side lumens, a rapid-exchange configuration having a single lumen proximal shaft and a guidewire port at some location along the shaft, or a fixed-wire configuration having a short flexible and non-moveable guidewire section affixed to the tip, and others. Also, the balloon catheter shaft 24 may preferably have a proximal shaft portion formed of a metal hypotube, as is explained below.

The sheath 20 is permanently mounted about the balloon catheter 12, yet able to slide a short distance longitudinally back and forth. The balloon catheter hub 22 provides fluid communication between the guidewire lumen 32 and guidewire coupling, as well as between the annular inflation lumen 30 and the inflation coupling. Of course, if the balloon catheter 12 has a fixed wire or rapid-exchange configuration, the balloon catheter hub 22 may not have a guidewire port 28 at all, but may rather have only an inflation port 26. The inner and outer tubular bodies 34 and 36 are securely received within the balloon catheter hub 22, and are surrounded by a tubular strain relief 40.

Figure 4:
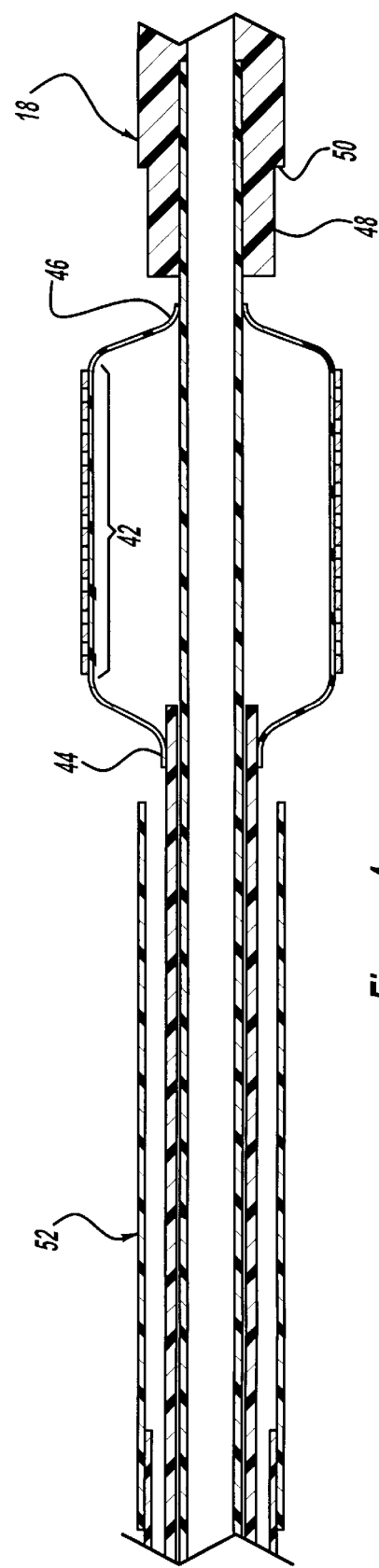
FIG. 4 is a partial longitudinal cross-section view of the stent delivery system of FIG. 3, wherein the balloon is inflated to expand the stent.
Figure 5:
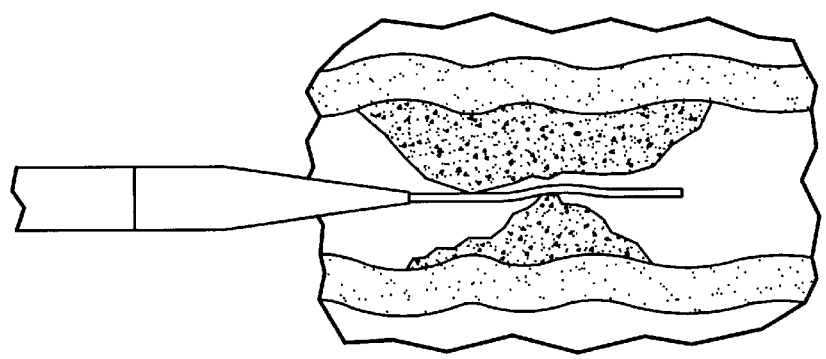
FIG. 5 is a partial side elevational view of a stent delivery system arranged according to the principles of the present invention, inserted to a location near a representative example of a desired treatment site.

When fully inflated as shown in FIG. 4, the balloon 16 has an inflated profile shape with a cylindrical working portion 42 having an inflated diameter located between a pair of conical end portions, and a pair of proximal and distal legs 44 and 46 affixed to the balloon catheter shaft 24. The balloon 16 in its deflated profile shape as shown in FIG. 1 preferably has several pleats wrapped around the balloon catheter shaft 24. The balloon material is preferably substantially inelastic, and stretches a relatively small amount under pressures of 15 atmospheres or more. Various different materials may be used, which preferably should be substantially inelastic. Some examples include Nylon, PEEK, Pebax, or a block copolymer thereof.

As shown in the drawings, the balloon 16 is preferably connected to the balloon catheter shaft 24 by affixing its distal end to the shaft inner tube 34, and its proximal end to the shaft outer tube 36. The balloon 16 thereby communicates with the annular inflation lumen 30 between the inner and outer shaft tubes 34 and 36. The balloon 16 may alternatively be attached to the balloon catheter shaft 24 in any way that allows it to be inflated with fluid from the inflation lumen 30.

The stent delivery system 10 of the present invention further has a flexible tapering introducer tip 18, adapted to help cross and traverse lesions or stenoses. Prior balloon catheter designs tend toward very small profiles at their distal tips, with the understanding that a small profile might assist in crossing a narrow lesion. This profile is simply defined by the outer diameter of the inner tube at its distal end, which may even be drawn down to an even smaller diameter. For example, in a coronary PTCA balloon catheter, the profile of the inner tube distal tip may range from about 0.040 to as small as 0.024. All dimension in this application are expressed in inches, except where indicated otherwise.

However, the stent delivery system 10 of the present invention instead tapers up to a much larger profile diameter, equal to the largest outer diameter of the sheath 20, which is slightly greater than the outer diameter of the crimped stent 14 itself. In the case of coronary direct stenting this preferred outer introducer tip 18 profile may range from about 0.047 to as much as 0.063, which is much greater than the diameter of the inner tube 34 distal profile. Indeed, the maximum diameter of the present introducer tip 18 may be more than twice that of the inner tube 34.

The introducer tip 18 may be affixed to the distal end of the inner tube 34 by any appropriate method that provides secure attachment, including an adhesive or by heat welding. The material selection of the introducer tip 18 should be selected such that it is more flexible than the distal end of the inner tube 34, even though the inner tube 34 is much smaller in diameter. This enhanced flexibility of the introducer tip 18 should preferably cooperate with the gently tapering slope to accurately follow the desired vascular path while minimizing the occurrence of any vascular trauma or complication, and tend to gently widen a stenosis or push aside thrombus.

Structurally, the introducer tip 18 as shown in the drawings preferably has a tapering conical main surface at its distal-most end, and a short cylindrical transition surface. The introducer tip 18 also has a short collar 48 with a slightly smaller outer diameter of preferably about 0.047–0.063, which defines a shoulder 50. The introducer tip 18 further defines a tip guidewire lumen 32 and a larger opening for receiving the distal end of the balloon catheter shaft inner body 34. The selection of material for the introducer tip 18 should be selected carefully, especially as far as its flexibility, preferably about 40–55D. The flexibility of the introducer tip 18 should be optimized to enable the stent delivery system 10 to accurately follow the guidewire 38 without causing prolapse.

Figure 10:
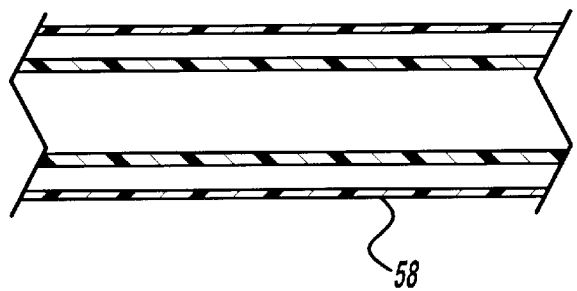
FIGS. 10 and 11 are partial cross-sectional views of alternative embodiments of the balloon catheter according to the present invention.
Figure 11:
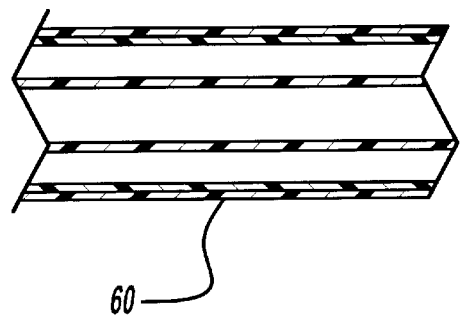

The sheath 20 includes a composite diameter sheath tube and a sheath hub 52 and 54. The sheath 20 is permanently mounted about the balloon catheter 12, but they are the generally free to slide longitudinally a short distance. To accomplish this feature, the sheath hub 54 allows the balloon catheter shaft 24 to slidably advance and withdraw through the sheath 20, and also preferably has a threaded screw-down locking device 56 for advancing the stent delivery system 10 as a single unit. As an alternative embodiment, a proximal portion of the balloon catheter shaft 24 may be formed or jacketed by a metal hypotube 58 or 60, as illustrated in FIGS. 10 and 11. This improvement allows the locking device 56 to clamp down on the balloon catheter shaft 24 without crushing it or blocking one of the lumens.

The sheath hub 54 preferably also has an injection port 62 for allowing radiopaque contrast fluid to be injected through the sheath tube 52 and around the balloon catheter shaft 24, thus illuminating the stent delivery system 10 on a fluoroscope. Rather than injecting through a guiding catheter (not shown), injecting radiopaque contrast through the sheath enables it to become visible when it extends distally beyond the guiding catheter.

The composite diameter sheath tube 52 includes at least a proximal and distal sheath tube 64 and 66. The proximal sheath tube 64 has a smaller diameter than the distal sheath tube 66. The minimum inner diameter of the distal sheath tube 66 is established by the crimped stent diameter, but the proximal sheath tube 64 may be smaller. The smaller proximal sheath 64 allows a higher volume and greater flow rate for injection of radiopaque contrast fluid through the guiding catheter and around the outside of the stent delivery system 10. This high-visibility feature enables the physician to selectively see the position of the stent delivery system 10 within the patient's body more easily.

A stent of any suitable type or configuration is preferably provided with the stent delivery system of the present invention, such as the well-known Palmaz-Schatz balloon expandable stent. Various kinds and types of stents are available in the market, and many different currently available stents are acceptable for use in the present invention, as well as new stents which may be developed in the future. The stent depicted in the drawings is a cylindrical metal stent having an initial crimped outer diameter, which may be forcibly expanded by the balloon to a deployed diameter. When deployed in a body passageway of a patient, the stent is preferably designed to press radially outward to hold the passageway open.

The distal end 68 of the sheath 20 fits snugly around the cylindrical collar 48 of the introducer tip 18 and abuts the shoulder 50. This distal end 68 of the sheath 20 thus can push against the shoulder 50 and assist in "pushability," which is an ability to push through or cross complicated vascular anatomy. The wall thickness of the sheath tube 52 should be selected to be thick enough to add acceptable pushability.

Figure 6:
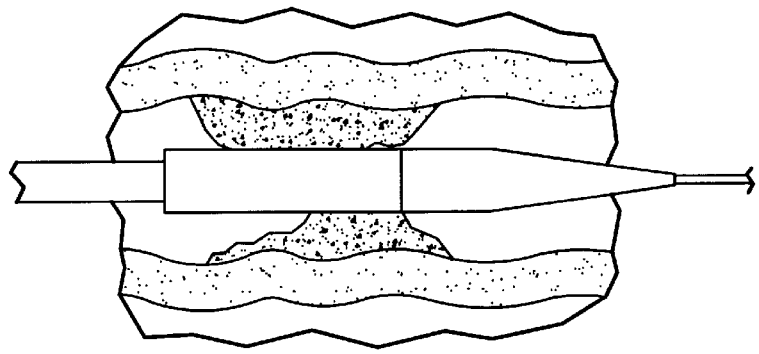
FIG. 6 is a partial side elevational view of the stent delivery system of FIG. 5, advanced to a desired position.

The operation of the stent delivery system is depicted in FIGS. 5–9, may be inserted percutaneously along a guidewire and within an outer guiding catheter (not shown), until the guiding catheter distal end reaches the vicinity of the desired site. The stent delivery system is then advanced wherein the stent delivery system as shown in FIG. 6 until the stent covered by the sheath is positioned within the lesion 74.

Figure 7:
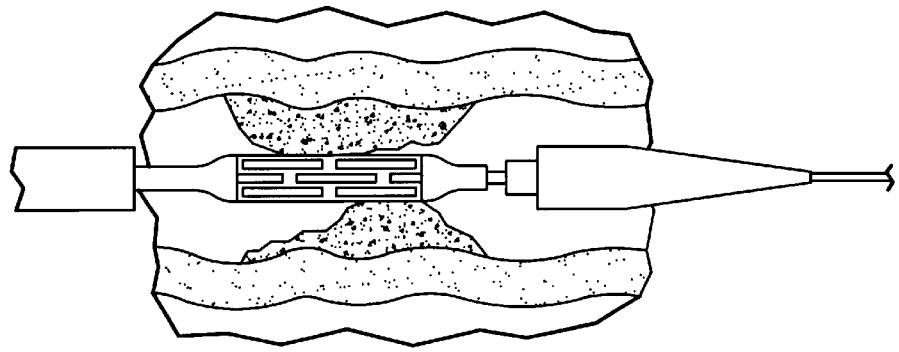
FIG. 7 is a partial side elevational view of the stent delivery system of FIG. 6, in which the sheath is partially retracted to uncover the stent.
Figure 8:
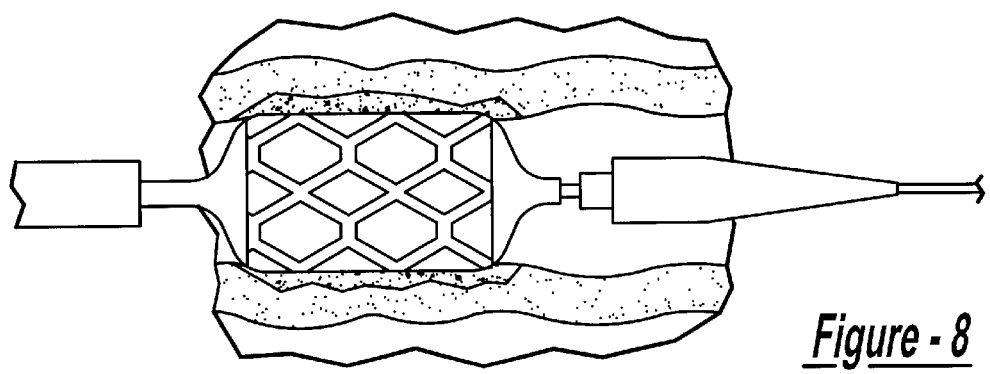
FIG. 8 is a partial side elevational view of the stent delivery system of FIG. 7, in which the balloon is inflated to expand the stent.
Figure 9:
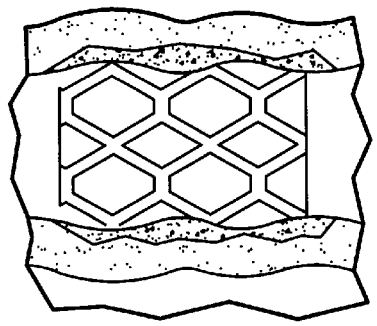
FIG. 9 is a partial side elevational view of a deployed stent, after removal of the stent delivery system.

The sheath is then partially retracted to uncover the stent as in FIG. 7. The balloon is inflated as in FIG. 8 to expand the stent, and the stent delivery system is removed from the patient's body as in FIG. 9, leaving the stent implanted at the desired site.

The balloon catheter system of the present invention may be made using any of the following methods, as well as various modifications that will be apparent to those skilled in the art.

Catheter manufacturing techniques are generally known in the art, including extrusion and co-extrusion, coating, adhesives, and molding. In particular for the present invention, the balloon catheter 12 may be made generally in a conventional manner. At some point before the introducer tip 18 is affixed to the distal end of the balloon catheter inner body, the sheath 20 is assembled onto the balloon catheter shaft 24. Then the stent 14 is crimped onto the balloon 16. After the introducer tip 18 is attached, the sheath 20 is advanced to cover the stent 14, and the finished assembly is packaged and sterilized.

Of course, the components of the present stent delivery system 10 invention may be constructed of various materials and have a range of acceptable dimensions.

The scope of the present invention encompasses the full extent of the claims, regardless of specific numbers, materials, or other details present in this description of the preferred embodiment.

Preferably, the balloon catheter hub 22 and the sheath hub 54 are injection molded of any suitable material. The inner and outer balloon catheter shaft tubes 34 and 36 are preferably made of a polymer such as Nylon, the material stiffness of which may be selected as appropriate.

One of the advantages of the present invention is the relatively small profile diameter that is possible along most of the length of the stent delivery system 10. Unless otherwise indicated, all dimensions are in inches. For example, the minimum crimped outer diameter of a stent may range from about 0.045–0.055. Each particular stent design of a particular expanded diameter will exhibit a minimum crimped diameter for several reasons, including that the stent struts or legs may overlap below that diameter.

In the case of a stent having a crimped outer diameter of 0.055, the sheath has a wall thickness of approximately 0.005 to as thin as 0.002, so the outer diameter of the distal sheath section is at most 0.060. On the tapered tip, the outer diameter and shoulder diameter match the outer and inner diameters of the distal sheath segment.

Because the diameter of the balloon catheter outer body is much less than that of the crimped stent, for example 0.033, the proximal sheath can also be smaller in diameter. For example, the proximal sheath segment might have a diameter of 0.045–0.050.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A stent deployment system, comprising:

a balloon catheter with an elongated flexible shaft having proximal and distal ends, a hub affixed to the shaft proximal end having a hub inflation port, and an inflatable balloon affixed to the shaft near the shaft distal end;

wherein the shaft defines an inflation lumen providing fluid communication of an inflation fluid between the hub inflation port and the balloon; at least a distal portion of the shaft having an inner member surrounded by an outer tube, at least a portion of the inflation lumen being defined by an annular space between the inner member and outer tube;

such that the balloon is adapted for selective inflation from a deflated state to an inflated state, as well as later deflation; the balloon being formed of a substantially inelastic material; the balloon having an inflated state with a cylindrical working portion located between a pair of proximal and distal conical portions, and a pair of proximal and distal leg portions; the proximal leg of the balloon being affixed to the outer tube, and the distal leg of the balloon being affixed to the inner member;

an expandable tubular stent mounted around the balloon and being crimped in an initial state about an outer surface of the deflated balloon;

a flexible introducer tip affixed to a distal end of the inner member, the introducer tip defining a relatively long conical surface tapering from a distal profile equal to or less than the inner member distal tip, up to a maximum profile, the introducer tip further defining a shoulder and collar; and a tubular sheath surrounding at least a portion of the balloon catheter outer tube, wherein the stent defines a crimped outer diameter in an initial state, the sheath having a proximal hub and a tubular sheath member, the tubular sheath member having a distal sheath portion with an inner diameter greater than the crimped outer diameter of the stent and being adapted to cover the stent in its initial state and an outer sheath diameter equal to the maximum profile, and a proximal sheath portion having a diameter less than said distal sheath portion, the sheath being partially retractable in a proximal direction to uncover the stent and enable the balloon to be inflated to expand the stent;

wherein a distal end of the tubular sheath member fits over the collar of the introducer tip, and is adapted to push on the shoulder of the introducer tip in a distal direction to enhance the pushability characteristic of the stent delivery system such that the stent delivery system achieves a primary stenting capability.

2. The balloon catheter stent deployment system of claim 1, wherein said stent is formed of an integral unitary metal cylinder having a plurality of apertures for allowing the stent to expand from the initial diameter to the deployed diameter.

3. The balloon catheter stent deployment system of claim 1, wherein said balloon is formed of a material selected from the group of Nylon, PEEK, Pebax, or a block copolymer thereof.

4. The balloon catheter stent deployment system of claim 1, further comprising a guidewire lumen defined by the inner member of the balloon catheter, extending from a guidewire port defined by the balloon catheter hub to a distal guidewire port at the balloon catheter distal end, adapted to slidably receive an elongated flexible guidewire.

5. The balloon catheter stent deployment system of claim 1, further comprising a locking device coupled with the sheath hub for selectively locking the sheath to the balloon catheter, near their proximal ends.

6. The balloon catheter stent deployment system of claim 1, further comprising a length of metal hypotube surrounding a proximal portion of the balloon catheter shaft to resist collapse of the balloon catheter shaft by the sheath locking device.

* * * * *